(12) United States Patent
Ryu et al.

(10) Patent No.: US 10,002,300 B2
(45) Date of Patent: Jun. 19, 2018

(54) APPARATUS AND METHOD FOR MONITORING DRIVER'S CONCENTRATIVENESS USING EYE TRACING

(71) Applicant: HYUNDAI MOTOR COMPANY, Seoul (KR)

(72) Inventors: Seong Sook Ryu, Seoul (KR); Byoung Joon Lee, Suwon-si (KR); Jin Kwon Kim, Suwon-si (KR); Ho Choul Jung, Suwon-si (KR); Sam Yong Kim, Hwaseong-si (KR)

(73) Assignee: Hyundai Motor Company, Seoul (KR)

( * ) Notice: Subject to any disclaimer, the term of this patent is extended or adjusted under 35 U.S.C. 154(b) by 92 days.

(21) Appl. No.: 15/333,584

(22) Filed: Oct. 25, 2016

(65) Prior Publication Data
US 2017/0364761 A1    Dec. 21, 2017

(30) Foreign Application Priority Data

Jun. 21, 2016 (KR) ........................ 10-2016-0077598

(51) Int. Cl.
*G06K 9/00* (2006.01)
*B60K 28/06* (2006.01)
*B60K 35/00* (2006.01)

(52) U.S. Cl.
CPC ........ *G06K 9/00845* (2013.01); *B60K 28/066* (2013.01); *B60K 35/00* (2013.01); *G06K 9/00604* (2013.01); *B60W 2540/26* (2013.01); *B60Y 2302/03* (2013.01); *B60Y 2400/90* (2013.01); *B60Y 2400/92* (2013.01)

(58) Field of Classification Search
CPC ............. B60K 28/066; B60K 35/00; B60W 2540/26; B60Y 2302/03; B60Y 2400/90; B60Y 2400/92; G06K 9/00604; G06K 9/00845
USPC ......................... 382/103, 104, 107
See application file for complete search history.

(56) References Cited

U.S. PATENT DOCUMENTS

| 2005/0209749 | A1  | 9/2005  | Ito et al. |
| 2010/0156617 | A1  | 6/2010  | Nakada et al. |
| 2010/0305755 | A1* | 12/2010 | Heracles ............ G06K 9/4671 700/253 |
| 2015/0339589 | A1* | 11/2015 | Fisher ................ G06N 99/005 706/12 |

(Continued)

FOREIGN PATENT DOCUMENTS

| JP | 2005-267108 A | 9/2005 |
| JP | 2007-329793 A | 12/2007 |

(Continued)

OTHER PUBLICATIONS

Korean Office Action issued in Application No. 10-2016-0077598 dated Nov. 21, 2017.

*Primary Examiner* — Tom Y Lu
(74) *Attorney, Agent, or Firm* — McDermott Will & Emery LLP

(57) ABSTRACT

Provided are an apparatus and method for monitoring driver's concentrativeness capable of monitoring whether a driver is concentratedly obtaining major information by tracing a driver's sight while a vehicle is running, in order to provide alarm to the driver when driver's concentrativeness is dropped at a time when the major information is changed while the vehicle is running.

20 Claims, 11 Drawing Sheets

(56) References Cited

U.S. PATENT DOCUMENTS

2017/0001648 A1* 1/2017 An .................. B60W 30/08

FOREIGN PATENT DOCUMENTS

| JP | 4625544 B2 | 2/2011 |
| JP | 2014-191474 A | 10/2014 |
| KR | 10-2013-0054830 A | 5/2013 |
| KR | 10-2013-0076218 A | 7/2013 |
| KR | 10-2014-0100629 A | 8/2014 |

* cited by examiner

FIG. 5

APPARATUS AND METHOD FOR MONITORING DRIVER'S CONCENTRATIVENESS USING EYE TRACING

CROSS-REFERENCE TO RELATED APPLICATION

This application is based on and claims the benefit of priority to Korean Patent Application No. 10-2016-0077598, filed on Jun. 21, 2016, in the Korean Intellectual Property Office, the disclosure of which is incorporated herein in its entirety by reference.

TECHNICAL FIELD

The present disclosure relates to an apparatus and method for monitoring driver's concentrativeness, and more particularly, to an apparatus and method for monitoring driver's concentrativeness using driver's eye tracing.

BACKGROUND

Most traffic accidents result from lack of responsiveness to situations due to drivers' carelessness and cognitive load. In contrast, drivers' drowsiness or unconscious state may cause a big accident but the number of cases is relatively small.

In particular, a driving pattern of a driver in a cognitive load state is not easily differentiated from a driving pattern of a concentrative operation state in a simple driving level, but when a driving environment is rapidly changed, a driver in the cognitive load state has a low response speed in response, which may end up with a traffic accident.

SUMMARY

The present disclosure has been made to solve the above-mentioned problems occurring in the prior art while advantages achieved by the prior art are maintained intact.

An aspect of the present disclosure provides an apparatus and method for monitoring driver's concentrativeness, capable of tracing driver's eyes, while a vehicle is running, to monitor whether the driver is concentratedly obtaining major information, in order to provide alarm when the driver's concentrativeness is dropped at the time when the major information is changed while the vehicle is running.

According to an exemplary embodiment of the present disclosure, an apparatus for monitoring driver's concentrativeness using eye tracing while a vehicle is running includes: a concentrativeness determiner determining in real time sight regions on which a driver keeps eyes while the vehicle is running and determining a sight concentrativeness value of each pixel corresponding to each sight region having a predetermined size in a front image to generate a concentrativeness map corresponding to the front image; a region of interest (ROI) determiner determining an ROI requiring driver's concentrativeness having a level equal to or higher than a predetermined level, relative to a peripheral comparison region, in the front image; and a concentrated state determiner determining whether the driver is in a concentrated state by comparing the ROI with the concentrativeness map corresponding to the front image.

The concentrativeness determiner may determine a sight concentrativeness value of each pixel that respectively sight concentrativeness values of pixels in each sight region are gradually reduced from a central vision portion positioned at the center of a sight direction of the driver to a peripheral vision portion therearound.

The concentrativeness determiner may configure the concentrativeness map by determining each sight region of each image frame, may generate the concentrativeness map by accumulating the sight concentrativeness value of each pixel during a predetermined number of frames, and may attenuate the sight concentrativeness value of each pixel in every predetermined number of frames.

The concentrativeness determiner may apply each weight value to a sight concentrativeness value of each pixel of a previous frame and a sight concentrativeness value of each pixel of a current frame and add up the sight concentrativeness values to accumulate the sight concentrativeness values.

The concentrativeness determiner may apply the same attenuation rate to the entire pixels in order to attenuate the sight concentrativeness values. The concentrativeness determiner may apply different attenuation rates according to a depth of each pixel on the basis of depth information of each pixel in order to attenuate the sight concentrativeness values.

The concentrated state determiner may determine that the driver is in a concentrated state, in response to a determination that an average of sight concentrativeness values of pixels of the ROI is equal to or greater than a threshold value.

The concentrated state determiner may determine that the driver is in a concentrated state, in response to a determination that sight concentrativeness values of pixels of the ROI are increased over time relative to concentrativeness values of the peripheral regions.

The concentrated state determiner may determine that the driver is in a concentrated state, in response to a determination that a distance between the center of pixels having a concentrativeness value equal to or greater than a threshold value and the center of the ROI is smaller than a predetermined value.

The concentrated state determiner may provide alarm to the driver through an interface, in response to a determination that the concentrated state of the driver is changed to a non-concentrated state.

According to another exemplary embodiment of the present disclosure, a method for monitoring driver's concentrativeness using eye tracing while a vehicle is running includes: determining in real time sight regions on which a driver keeps eyes while the vehicle is running and determining a sight concentrativeness value of each pixel corresponding to each sight region having a predetermined size in a front image to generate a concentrativeness map corresponding to the front image; determining an ROI requiring driver's concentrativeness having a level equal to or higher than a predetermined level, relative to a peripheral comparison region, in the front image; and determining whether the driver is in a concentrated state by comparing the ROI with the concentrativeness map corresponding to the front image.

The generating of the concentrativeness map may include determining the sight concentrativeness value of each pixel that respective sight concentrativeness values of pixels in each sight region are gradually reduced from a central vision portion positioned at the center of a sight direction of the driver to a peripheral vision portion therearound.

The generating of the concentrativeness map may include configuring the concentrativeness map by determining each sight region of each image frame, generating the concentrativeness map by accumulating the sight concentrativeness value of each pixel during a predetermined number of frames, and attenuating the sight concentrativeness value of each pixel in every predetermined number of frames.

Each weight value may be applied to a sight concentrativeness value of each pixel of a previous frame and a sight concentrativeness value of each pixel of a current frame and the sight concentrativeness values may be added up to accumulate the sight concentrativeness values.

The same attenuation rate may be applied to the entire pixels in order to attenuate the sight concentrativeness values.

Different attenuation rates may be applied according to a depth of each pixel on the basis of depth information of each pixel in order to attenuate the sight concentrativeness values.

The determining of whether the driver is in a concentrated state may include determining, in response to a determination that an average of sight concentrativeness values of pixels of the ROI is equal to or greater than a threshold value, that the driver is in a concentrated state.

The determining of whether the driver is in a concentrated state may include determining, in response to a determination that sight concentrativeness values of the pixels of the ROI are increased over time, relative to concentrativeness values of the peripheral regions, that the driver is in a concentrated state.

The determining of whether the driver is in a concentrated state may include determining, in response to a determination that a distance between the center of pixels having a concentrativeness value equal to or greater than a threshold value and the center of the ROI is smaller than a predetermined value, that the driver is in a concentrated state.

The determining of whether the driver is in a concentrated state may include: providing, in response to a determination that the concentrated state of the driver is changed to a non-concentrated state, alarm to the driver through an interface.

BRIEF DESCRIPTION OF THE DRAWINGS

The above and other objects, features and advantages of the present disclosure will be more apparent from the following detailed description taken in conjunction with the accompanying drawings.

FIG. 5 is a view illustrating attenuation of each pixel of a sight concentrativeness map by frame in the present disclosure.

DETAILED DESCRIPTION

Figure 1:
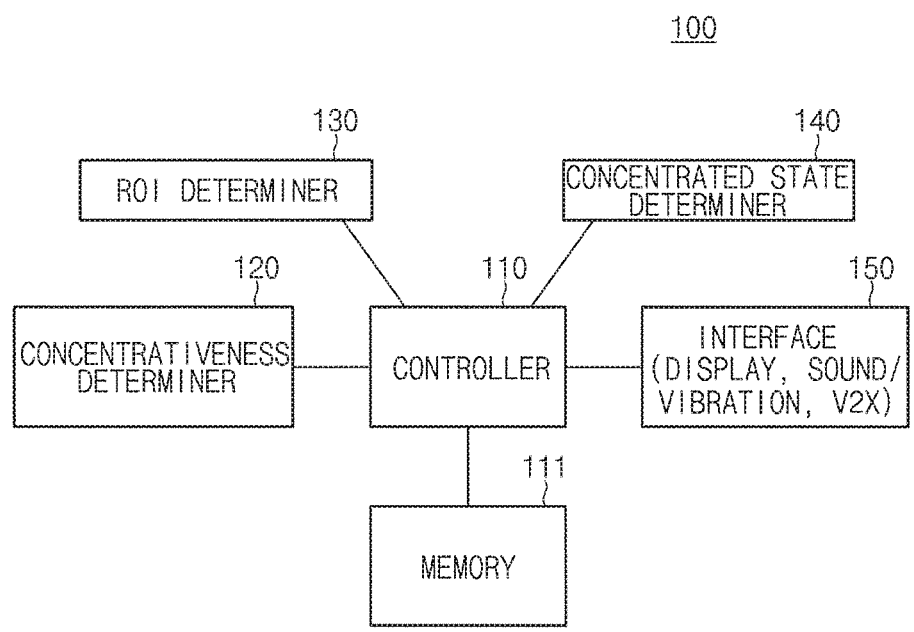
FIG. 1 is a block diagram illustrating an apparatus for monitoring driver's concentrativeness according to an exemplary embodiment of the present disclosure.

Hereinafter, exemplary embodiments of the present disclosure will be described in detail with reference to the accompanying drawings. In this case, in each drawing, like reference numerals refer to like elements. Also, the detailed descriptions of the relevant known functions and/or configurations are omitted. In the below-disclosed details, descriptions will focus on elements necessary to understand operations according to various embodiments, and the detailed descriptions on elements which unnecessarily obscure the important points of the descriptions will be omitted. Also, in the drawings, some elements may be exaggerated, omitted, or schematically illustrated. The size of each element does not entirely reflect an actual size, and thus, details described herein are not limited by the relative sizes or interval of elements illustrated in each drawing.

FIG. 1 is a block diagram illustrating an apparatus 100 for monitoring driver's concentrativeness according to an exemplary embodiment of the present disclosure.

Referring to FIG. 1, the apparatus 100 for monitoring driver's concentrativeness using driver's eye tracing according to an exemplary embodiment of the present disclosure includes a controller 110, a memory 111, a concentrativeness determiner 120, a region of interest (ROI) determiner 130, a concentrated state determiner 140, and an interface 150.

The components of the apparatus 100 for monitoring driver's concentrativeness using driver's eye tracing according to an exemplary embodiment of the present disclosure that may be mounted in a vehicle may be implemented by hardware such as a semiconductor processor, software such as an application program, or a combination thereof. Also, the controller 110 performing general controlling of various components of the apparatus 100 may be implemented to include a function of one or more of the other components, and a partial function of the controller 110 may be implemented as a separate component as another unit. The memory 111 stores data or configuration information required for an operation of the apparatus 100 for monitoring driver's concentrativeness.

First, an operation of the apparatus 100 for monitoring driver's concentrativeness according to an exemplary embodiment of the present disclosure will be described.

The concentrativeness determiner 120 determines a sight region regarding a front side that a driver keeps eyes in every image frame in real time while a vehicle is running and determines a sight concentrativeness value of each pixel corresponding to each sight region having a predetermined size in a front image to generate a concentrativeness map corresponding to the entire front image. Here, the concentrativeness determiner 120 may determine a sight region regarding a front side on which the driver keeps eyes by analyzing an image regarding the driver captured by and transmitted from an image capture device such as a camera, or the like, mounted in the vehicle. Also, the concentrativeness determiner 120 may search for each sight region (please refer to FIGS. 3 and 4) from another front image of the vehicle captured by and transmitted from another image capture device and determine a sight concentrativeness value of each of corresponding pixels.

The ROI determiner 130 determines an ROI (please refer to FIGS. 7A, 7B, and 7C) requiring driver's concentrativeness having a level equal to or higher than a predetermined level, relative to a peripheral comparison region in the front image.

The concentrated state determiner 140 compares a concentrativeness map corresponding to the front image with the ROI to determine a concentrated state (concentration/non-concentration) of the driver. Also, when the concentrated state determiner 140 determines that the concentrated state of the driver is changed to a non-concentrated state, the concentrated state determiner 140 may provide alarm to the driver through the interface 150.

For example, the interface 150 may include a display device supporting a liquid crystal display (LCD), a head-up display (HUD), augmented reality (AR), and the like, may include a notification means that is able to physically contact the driver such as a sound, vibration, illumination, a temperature, and the like, and may include a means supporting vehicle-to-anything (V2X) communication with the exterior. According to circumstances, the interface 150 may also include a control device for controlling a vehicle, such as a brake, a steering system, and the like.

When the concentrated state determiner 140 determines that driver's concentrativeness on an ROI, or the like, is dropped, the concentrated state determiner 140 may provide an alarm service, or the like, to the driver on the basis of the driver's current fatigue state, carelessness event occurrence history, a degree of drowsiness, a change in feeling, or road situation information through V2X communication through the interface 150. For example, through the interface 150, the concentrated state determiner 140 may provide physical contact notification by a means that can physically come into contact with the driver such as a sound, vibration, illumination, and a temperature, may provide a guidance or interactive message indicating the need of a break to a display device, or may provide a service such as braking, steering, and the like, in accordance with a concentrated state of the driver through a control device for controlling the vehicle. The control device for controlling the vehicle may use information from a vehicle sensor, such as information of a distance to a preceding vehicle using a radar sensor, vehicle speed information using a wheel speed sensor/acceleration/deceleration pedal sensor, to control braking or steering.

Hereinafter, an operation of the apparatus 100 for monitoring driver's concentrativeness according to an exemplary embodiment of the present disclosure will be described in more detail with reference to the flow chart of FIG. 2.

Figure 2:
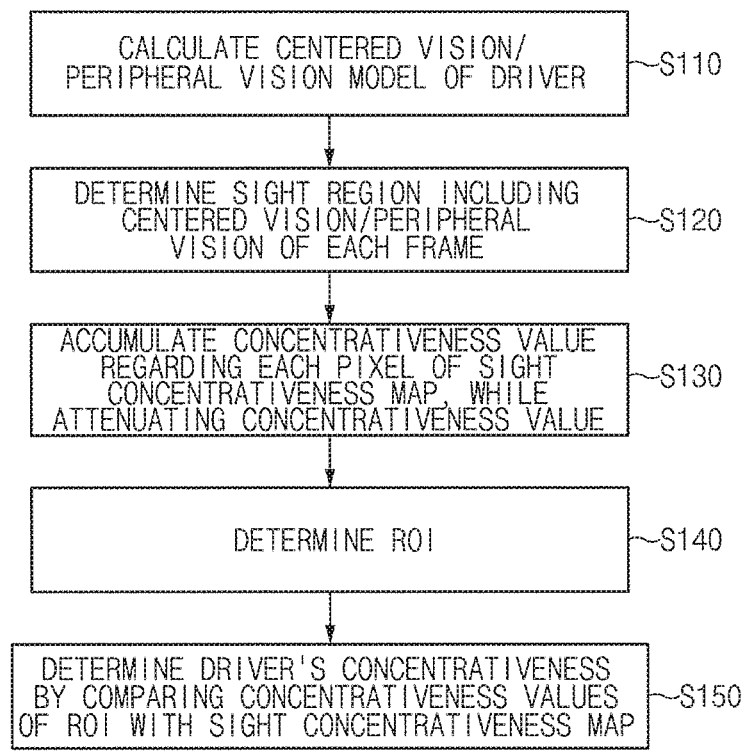
FIG. 2 is a flow chart illustrating an operation of an apparatus for monitoring driver's concentrativeness according to an exemplary embodiment of the present disclosure.

FIG. 2 is a flow chart illustrating an operation of the apparatus 100 for monitoring driver's concentrativeness according to an exemplary embodiment of the present disclosure.

Figure 3:
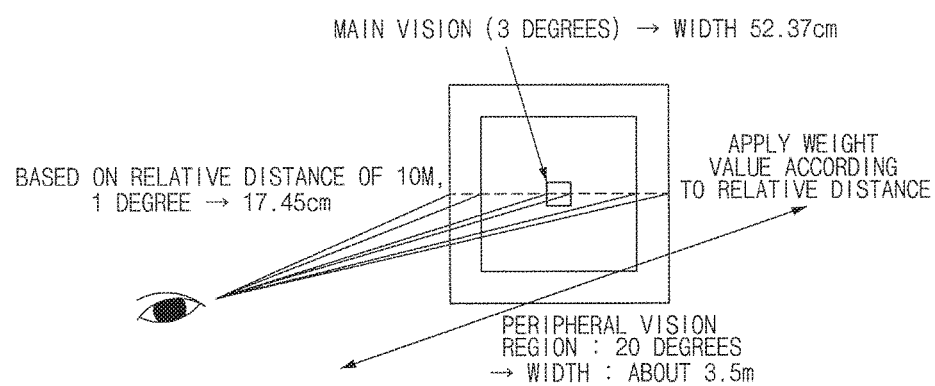
FIG. 3 is a view illustrating a central vision/peripheral vision model of the present disclosure.

Referring to FIG. 2, first, in order to determine a sight region regarding a front side on which the driver keeps eyes and generate a concentrativeness map while the vehicle is running, the concentrativeness determiner 120 calculates a central vision and peripheral vision model of the driver according to a sight model predefined on the basis of a general eyeball model as illustrated in FIG. 3 in operation S110. That is, the concentrativeness determiner 120 may determine a region from a central vision portion positioned at the center in the sight direction of the driver to a peripheral vision portion therearound, as a sight region in operation S120. For example, in a case in which a person having a normal vision of 1.0 is defined to have a main vision of 3 degrees, a region of the 3 degrees of the main vision may be considered by the concentrativeness determiner 120 as a central vision portion and a region therearound up to 20 degrees may be considered by the concentrativeness determiner 120 as a peripheral vision portion. Since each person may have a different main vision, the concentrativeness determiner 120 may determine a sight region of each person by reflecting a weight value for each person according to a relative distance with respect to a front side.

When the concentrativeness determiner 120 determines the sight region on the basis of the central vision and peripheral vision model of the driver, the concentrativeness determiner 120 may generate a concentrativeness map corresponding to the entire front image by determining a sight concentrativeness value of each pixel corresponding to each sight region.

Figure 4:
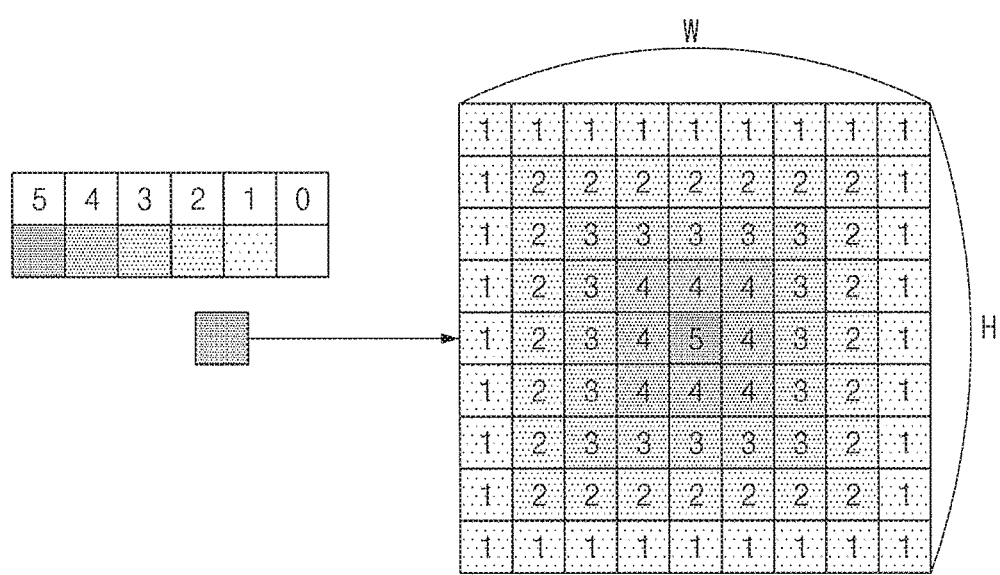
FIG. 4 is a view illustrating determination regarding a sight region of the present disclosure.

For example, as illustrated in FIG. 4, the concentrativeness determiner 120 may determine a sight concentrativeness value of each pixel that sight concentrativeness values of pixels are gradually reduced from the central vision portion positioned at the center of the sight direction of the driver to a peripheral vision portion therearound in each sight region of each image frame. FIG. 4 illustrates an example of sight concentrativeness values of respective pixels of the sight region determined by the concentrativeness determiner 120 such that a concentrativeness value of the central vision portion is indicated by 5 and concentrativeness values of the peripheral vision portions therearound are reduced to 4, 3, 2, and 1 in the rectangular W*H sight region (W and H are natural numbers).

The concentrativeness determiner 120 accumulates the concentrativeness values regarding each pixel of the concentrativeness map corresponding to the entire front image, while attenuating the same on the basis of the image frame, in operation S130. The concentrativeness determiner 120 may determine a concentrativeness value of each pixel at each stage of sight concentrativeness according to accumulation and an attenuation rate of each stage of sight concentrativeness in each frame.

The concentrativeness determiner 120 may configure the concentrativeness map by determining each sight region of each image frame, and may repeat a process of generating a concentrativeness map by accumulating a sight concentrativeness value of each pixel during a predetermined number of frames (i.e., three frames) and attenuating the sight concentrativeness value of each pixel in every predetermined number of frames (e.g., three frames). Here, the sight concentrativeness values may be accumulated and subsequently attenuated, or attenuated and subsequently accumulated by the concentrativeness determiner 120.

Figure 5:
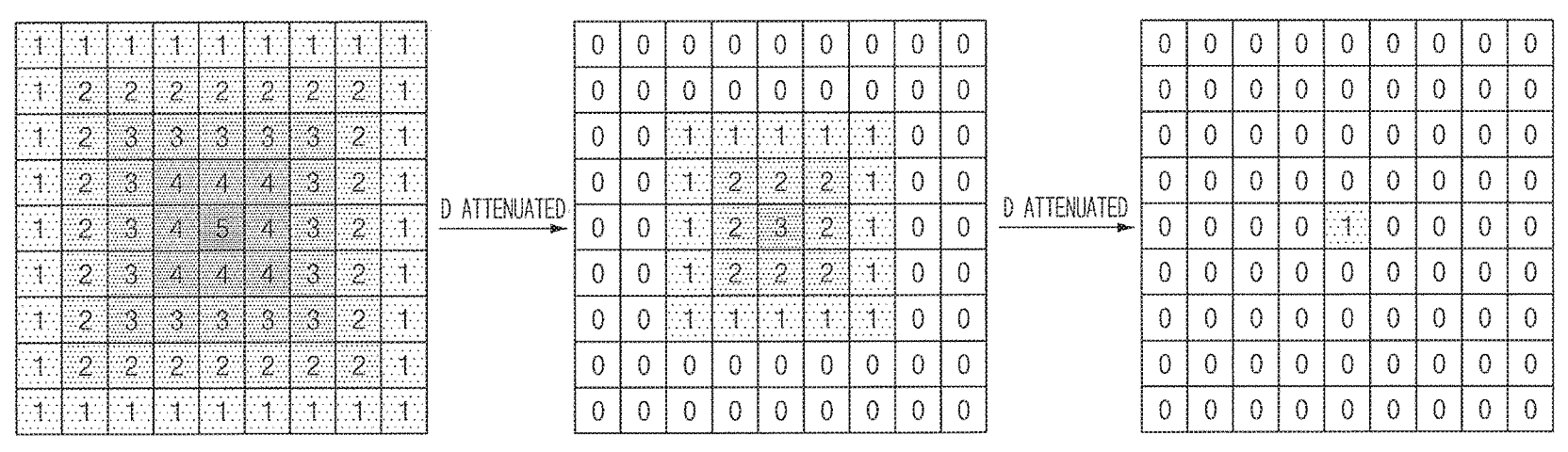

For example, as illustrated in FIG. 5, to attenuate the sight concentrativeness value of each pixel of the current concentrativeness map in every predetermined number of frames (e.g., three frames), the concentrativeness determiner 120 may apply the same attenuation rate (e.g., reduction by D=2 each time) to the entire pixels. In some circumstances, the concentrativeness determiner 120 may attenuate the sight concentrativeness value of each pixel of the current concentrativeness map in every predetermined number of frames (e.g., three frames) and apply different attenuation rates according to a depth of each pixel on the basis of depth information per pixel based on a 3D camera, or the like. Here, a greater attenuation rate may be applied to a pixel having a greater depth value than to a pixel having a smaller depth value.

Figure 6:
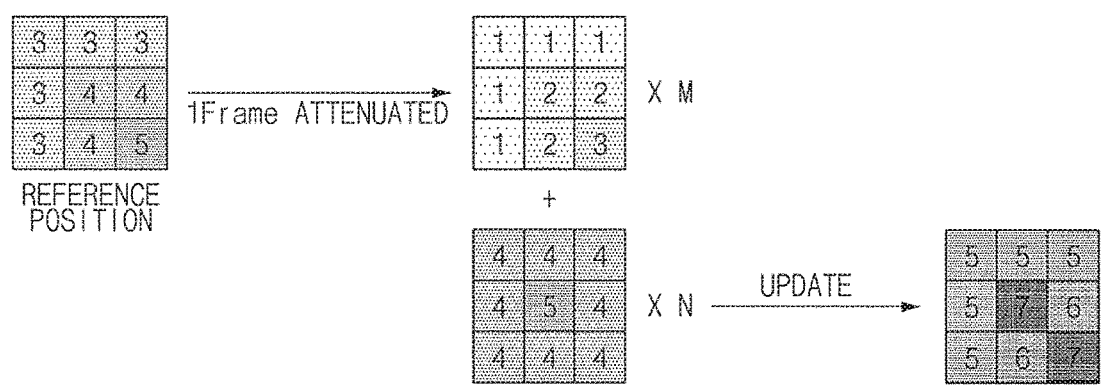
FIG. 6 is a view illustrating accumulation of each pixel of a sight concentrativeness map by frame in the present disclosure.

FIG. 6 is a view illustrating accumulation of each pixel of a sight concentrativeness map by frame in the present disclosure.

As illustrated in FIG. 6, to generate a concentrativeness map by accumulating the sight concentrativeness value of each pixel during a predetermined number of frames, the concentrativeness determiner 120 may apply each weight value to a sight concentrativeness value of each pixel of a previous frame and a sight concentrativeness value of each pixels of a current frame and add up the concentrativeness values to generate a concentrativeness value-accumulated concentrativeness map. FIG. 6 illustrates an example of accumulating concentrativeness values during two frames (previous frame and current frame) in which M=1 is a weight value of a sight concentrativeness value of the previous frame and N=1 is a weight value of a sight concentrativeness value of the current frame. Even when concentrativeness values of three or more frames are accumulated, the concentrativeness values may be accumulated by applying the same weight value or different weight values to respective frames.

Figure 7A:
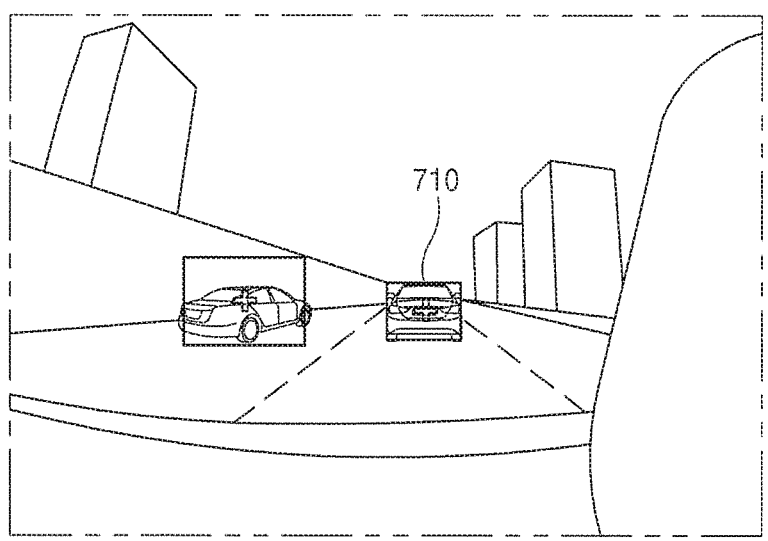
FIGS. 7A to 7C are views illustrating determination of a region of interest (ROI) in the present disclosure.
Figure 7B:
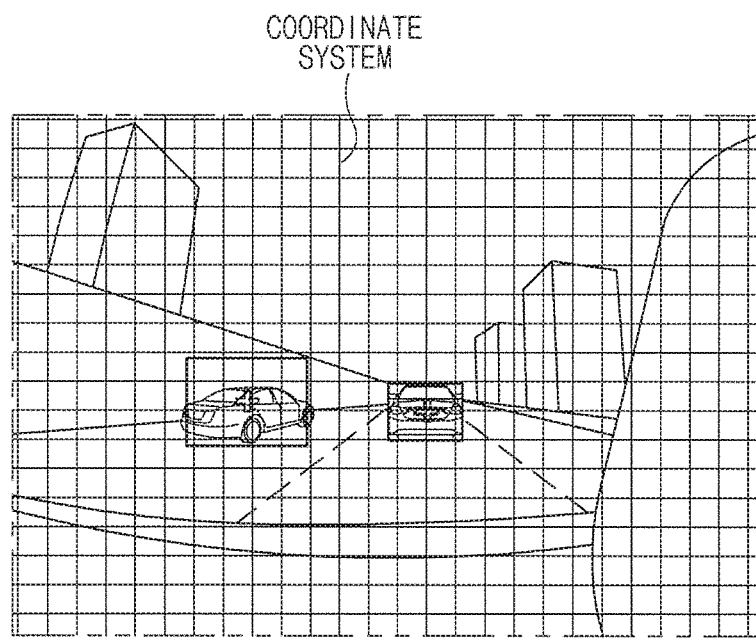
Figure 7C:
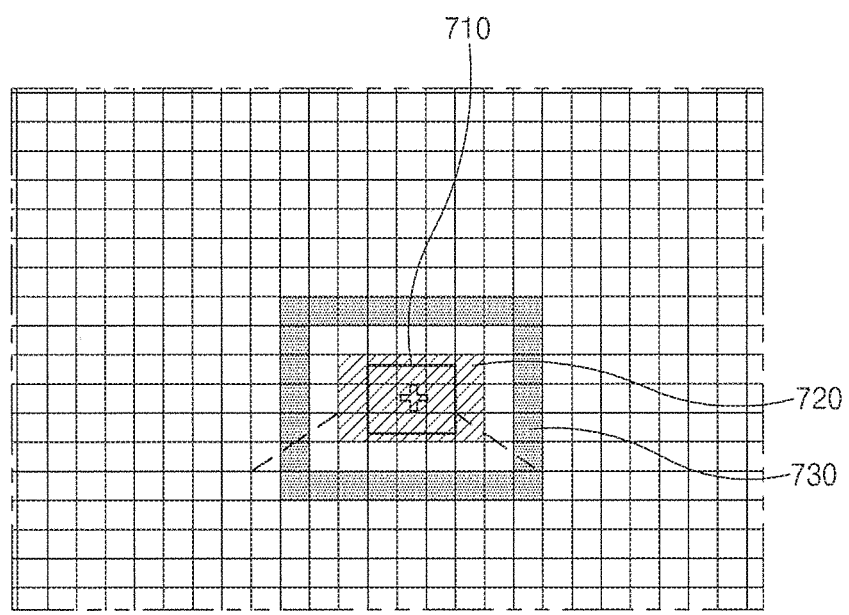

The ROI determiner 130 determines an ROI (please refer to FIGS. 7A, 7B, and 7C) requiring driver's concentrativeness having a level equal to or higher than a predetermined level, compared with a peripheral comparison region (reference region for comparison) in a front image in operation S140. The ROI determiner 130 may analyze feature points of the image of the front side of the vehicle to detect valid objects affecting an influence on driving of the driver's vehicle, such as a lane in which the vehicle is running, a preceding vehicle, traffic sign, a signal light, an obstacle, and the like. For example, when a preceding vehicle is detected as illustrated in FIG. 7A, the ROI determiner 130 matches a preceding vehicle region 710 to coordinates of the concentrativeness map on the basis of a predetermined coordinate system such as a vehicle coordinate system, or the like, as illustrated in FIG. 7B, determines a predetermined extended region including the preceding vehicle region 710 as an ROI 720 as illustrated in FIG. 7C, and sets the ROI 720 as a region requiring driver's concentrativeness having a level equal to or higher than the predetermined level, compared with the peripheral comparison region (region for comparison) 730.

The concentrated state determiner 140 determines a concentrated state (concentration/non-concentration) of the driver by comparing the ROI with the concentrativeness map corresponding to the front image in operation S150. Also, when the concentrated state determiner 140 determines that a concentrated state of the driver is changed to a non-concentrated state, the concentrated state determiner 140 may provide alarm to the driver according to various methods as mentioned above through the interface 150.

For example, when an average of sight concentrativeness values of pixels of the ROI (e.g., 720) is equal to or greater than a threshold value, the concentrated state determiner 140 may determine that the driver is in a concentrated state.

Also, when sight concentrativeness values of the pixels of the ROI (e.g., 720) are increased over time, relative to concentrativeness values of the peripheral regions, the concentrated state determiner 140 may determine that the driver is in a concentrated state.

Figure 8:
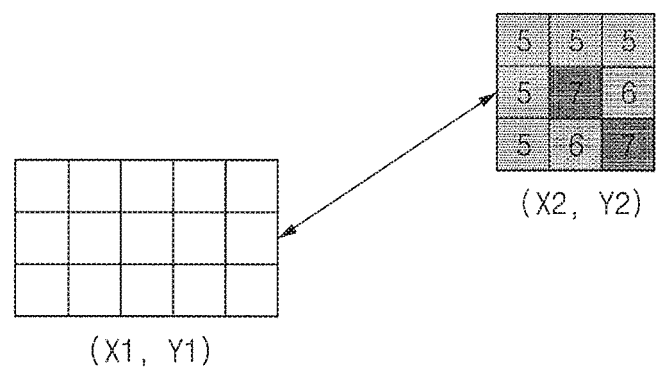
FIG. 8 is a view illustrating an example of determining driver's concentrativeness in the present disclosure.

Also, as illustrated in FIG. 8, when a distance between the center (X1,Y1) of pixels having a concentrativeness value equal to or greater than a threshold value and the center (X2, Y2) of the ROI is smaller than a predetermined value, the concentrated state determiner 140 may determine that the driver is in a concentrated state. To this end, the concentrated state determiner 140 may detect a group of one or more pixels (e.g., a rectangular shape) each having a concentrativeness value equal to or greater than the threshold value and calculate central coordinates (X1, Y1) of each pixel of the group to calculate a distance between the central coordinate (X1, Y1) of each pixel and the central coordinates (X2, Y2) of the ROI.

Figure 9:
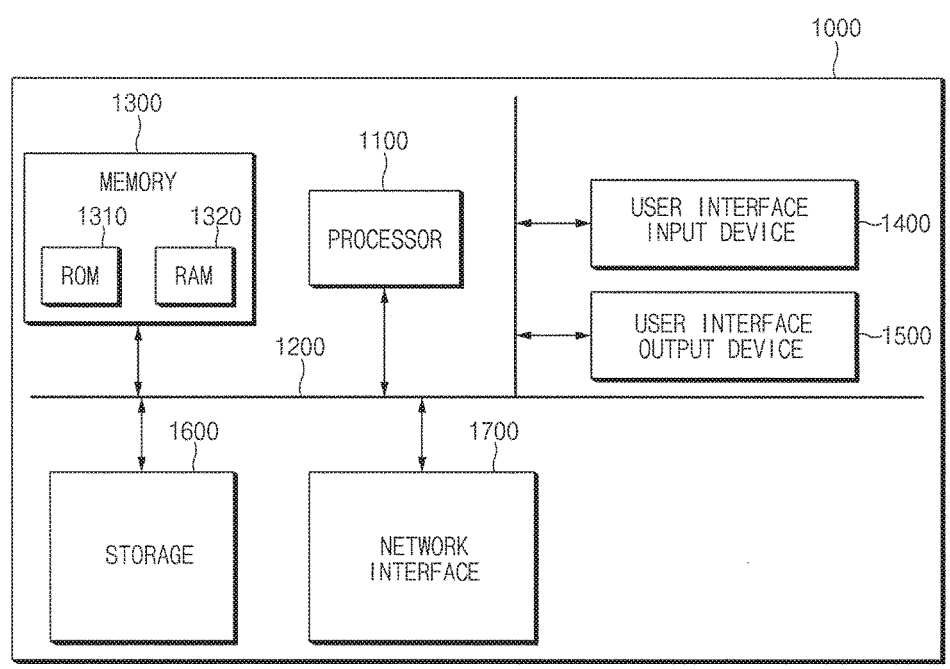
FIG. 9 is a view illustrating an example for implementing an apparatus for monitoring driver's concentrativeness according to an exemplary embodiment of the present disclosure.

FIG. 9 is a view illustrating an example for implementing the apparatus 100 for monitoring driver's concentrativeness according to an exemplary embodiment of the present disclosure. The apparatus 100 for monitoring driver's concentrativeness according to an exemplary embodiment of the present disclosure may be configured by hardware, software, or a combination thereof. For example, the apparatus 100 for monitoring driver's concentrativeness according to an exemplary embodiment of the present disclosure may be implemented as a computing system 1000 illustrated in FIG. 9.

The computing system 1000 may include at least one processor 1100, a memory 1300, a user interface input device 1400, a user interface output device 1500, a storage 1600, and a network interface 1700 connected through a bus 1200. The processor 1100 may be a semiconductor device executing processing on command languages stored in a central processing unit (CPU) or the memory 1300 and/or storage 1600. The memory 1300 and the storage 1600 may include various types of volatile or nonvolatile storage mediums. For example, the memory 1300 may include a read only memory (ROM) 1310 and a random access memory (RAM) 1320.

Thus, the steps of the method or algorithm described above in relation to the exemplary embodiments of the present disclosure may be directly implemented by hardware, a software module, or a combination thereof executed by the processor 1100. The software module may reside in a storage medium (i.e., the memory 1300 and/or the storage 1600) such as a RAM memory, a flash memory, a ROM memory, an EPROM memory, an EEPROM memory, a register, a hard disk, a detachable disk, or a CD-ROM. An exemplary storage medium is coupled to the processor 1100, and the processor 1100 may read information from the storage medium and write information into the storage medium. In another embodiment, the storage medium may be integrated with the processor 1100. The processor 1100 and the storage medium may reside in an application specific integrated circuit (ASIC). The ASIC may reside in a user terminal. In another embodiment, the processor 1100 and the storage medium may reside as separate components in a user terminal.

As described above, in the apparatus and method for monitoring driver's concentrativeness according to exemplary embodiments of the present disclosure, by monitoring whether a driver is concentratedly obtaining major information by tracing driver's eyes while the vehicle is running, alarm may be effectively provided to the driver when driver's concentrativeness is dropped at a time when the major information is changed while the vehicle is running.

Hereinabove, although the present disclosure has been described with reference to exemplary embodiments and the accompanying drawings, the present disclosure is not limited thereto, but may be variously modified and altered by those skilled in the art to which the present disclosure pertains without departing from the spirit and scope of the present disclosure claimed in the following claims.

What is claimed is:
1. An apparatus for monitoring driver's concentrativeness using eye tracing while a vehicle is running, the apparatus comprising:
 a concentrativeness determiner determining in real time sight regions on which a driver keeps eyes while the vehicle is running and determining a sight concentrativeness value of each pixel corresponding to each sight region having a predetermined size in a front image to generate a concentrativeness map corresponding to the front image;

a region of interest (ROI) determiner determining an ROI requiring driver's concentrativeness having a level equal to or higher than a predetermined level, relative to a peripheral comparison region, in the front image; and a concentrated state determiner determining whether the driver is in a concentrated state by comparing the ROI with the concentrativeness map corresponding to the front image.

2. The apparatus according to claim 1, wherein the concentrativeness determiner determines a sight concentrativeness value of each pixel that respective sight concentrativeness values of pixels in each sight region are gradually reduced from a central vision portion positioned at the center of a sight direction of the driver to a peripheral vision portion therearound.

3. The apparatus according to claim 1, wherein the concentrativeness determiner configures the concentrativeness map by determining each sight region of each image frame, generates the concentrativeness map by accumulating the sight concentrativeness value of each pixel during a predetermined number of frames, and attenuates the sight concentrativeness value of each pixel in every predetermined number of frames.

4. The apparatus according to claim 3, wherein the concentrativeness determiner applies each weight value to a sight concentrativeness value of each pixel of a previous frame and a sight concentrativeness value of each pixel of a current frame and adds up the sight concentrativeness values to accumulate the sight concentrativeness values.

5. The apparatus according to claim 3, wherein the concentrativeness determiner applies the same attenuation rate to the entire pixels to attenuate the sight concentrativeness values.

6. The apparatus according to claim 3, wherein the concentrativeness determiner applies different attenuation rates according to a depth of each pixel on the basis of depth information of each pixel to attenuate the sight concentrativeness values.

7. The apparatus according to claim 1, wherein the concentrated state determiner determines that the driver is in a concentrated state, in response to a determination that an average of sight concentrativeness values of pixels of the ROI is equal to or greater than a threshold value.

8. The apparatus according to claim 1, wherein the concentrated state determiner determines that the driver is in a concentrated state, in response to a determination that sight concentrativeness values of pixels of the ROI are increased over time relative to concentrativeness values of the peripheral regions.

9. The apparatus according to claim 1, wherein the concentrated state determiner determines that the driver is in a concentrated state, in response to a determination that a distance between the center of pixels having a concentrativeness value equal to or greater than a threshold value and the center of the ROI is smaller than a predetermined value.

10. The apparatus according to claim 1, wherein the concentrated state determiner provides alarm to the driver through an interface, in response to a determination that the concentrated state of the driver is changed to a non-concentrated state.

11. A method for monitoring driver's concentrativeness using eye tracing while a vehicle is running, the method comprising:

determining in real time sight regions on which a driver keeps eyes while the vehicle is running and determining a sight concentrativeness value of each pixel corresponding to each sight region having a predetermined size in a front image to generate a concentrativeness map corresponding to the front image;

determining an ROI requiring driver's concentrativeness having a level equal to or higher than a predetermined level, relative to a peripheral comparison region, in the front image; and determining whether the driver is in a concentrated state by comparing the ROI with the concentrativeness map corresponding to the front image.

12. The method according to claim 11, wherein the generating of the concentrativeness map comprises: determining the sight concentrativeness value of each pixel that respective sight concentrativeness values of pixels in each sight region are gradually reduced from a central vision portion positioned at the center of a sight direction of the driver to a peripheral vision portion therearound.

13. The method according to claim 11, wherein the generating of the concentrativeness map comprises: configuring the concentrativeness map by determining each sight region of each image frame, generating the concentrativeness map by accumulating the sight concentrativeness value of each pixel during a predetermined number of frames, and attenuating the sight concentrativeness value of each pixel in every predetermined number of frames.

14. The method according to claim 13, wherein each weight value is applied to a sight concentrativeness value of each pixel of a previous frame and a sight concentrativeness value of each pixel of a current frame and the sight concentrativeness values are added up to accumulate the sight concentrativeness values.

15. The method according to claim 13, wherein the same attenuation rate is applied to the entire pixels in order to attenuate the sight concentrativeness values.

16. The method according to claim 13, wherein different attenuation rates are applied according to a depth of each pixel on the basis of depth information of each pixel in order to attenuate the sight concentrativeness values.

17. The method according to claim 11, wherein the determining of whether the driver is in a concentrated state comprises: determining, in response to a determination that an average of sight concentrativeness values of pixels of the ROI is equal to or greater than a threshold value, that the driver is in a concentrated state.

18. The method according to claim 11, wherein the determining of whether the driver is in a concentrated state comprises: determining, in response to a determination that sight concentrativeness values of the pixels of the ROI are increased over time relative to concentrativeness values of the peripheral regions, that the driver is in a concentrated state.

19. The method according to claim 11, wherein the determining of whether the driver is in a concentrated state comprises: determining, in response to a determination that a distance between the center of pixels having a concentrativeness value equal to or greater than a threshold value and the center of the ROI is smaller than a predetermined value, that the driver is in a concentrated state.

20. The method according to claim 11, wherein the determining of whether the driver is in a concentrated state includes: providing, in response to a determination that the concentrated state of the driver is changed to a non-concentrated state, alarm to the driver through an interface.

* * * * *